(12) United States Patent
Shimoda et al.

(10) Patent No.: US 9,478,090 B2
(45) Date of Patent: Oct. 25, 2016

(54) IMAGE SENSOR UNIT, IMAGE READING APPARATUS, AND PAPER SHEET DISTINGUISHING APPARATUS

(71) Applicant: CANON COMPONENTS, INC., Saitama (JP)

(72) Inventors: Shuuichi Shimoda, Saitama (JP); Junya Kinoshita, Saitama (JP); Yoshio Kureishi, Saitama (JP); Ryoki Matsui, Saitama (JP); Hidemasa Yoshida, Saitama (JP); Yoshihiko Tsumekawa, Saitama (JP); Hidehisa Takahashi, Saitama (JP); Akifumi Fujiwara, Saitama (JP); Suguru Tashiro, Saitama (JP); Takashi Chiba, Saitama (JP)

(73) Assignee: CANON COMPONENTS, INC., Saitama (JP)

( * ) Notice: Subject to any disclaimer, the term of this patent is extended or adjusted under 35 U.S.C. 154(b) by 0 days.

(21) Appl. No.: 14/519,762

(22) Filed: Oct. 21, 2014

(65) Prior Publication Data
US 2015/0110382 A1 Apr. 23, 2015

(30) Foreign Application Priority Data

Oct. 22, 2013 (JP) .................................. 2013-219626
Oct. 9, 2014 (JP) .................................. 2014-208144

(51) Int. Cl.
*G06K 9/00* (2006.01)
*G07D 7/12* (2016.01)
(Continued)

(52) U.S. Cl.
CPC .............. *G07D 7/121* (2013.01); *G01N 21/86* (2013.01); *G01N 21/8806* (2013.01); *G01N 21/8914* (2013.01); *G07D 7/2025* (2013.01);
(Continued)

(58) Field of Classification Search
None
See application file for complete search history.

(56) References Cited

U.S. PATENT DOCUMENTS

| 8,964,262 B2 | 2/2015 | Shimoda |
| 2005/0150956 A1 | 7/2005 | Ikeda et al. |

(Continued)

FOREIGN PATENT DOCUMENTS

| JP | 2005198106 A | 7/2005 |
| JP | 2006166106 A | 6/2006 |

(Continued)

OTHER PUBLICATIONS

Japanese Office Action issued in Japanese counterpart application No. JP2014-208144, dated Jun. 30, 2015.

*Primary Examiner* — Hadi Akhavannik
(74) *Attorney, Agent, or Firm* — Rossi, Kimms & McDowell LLP

(57) ABSTRACT

An image sensor unit includes: a plurality of light sources each including an LED chip; a plurality of light guides that are arranged in parallel to face incident surfaces on one side in a longitudinal direction for each of the plurality of light sources and that guide light from the plurality of light sources to a bill; an image sensor that converts light from the bill to an electric signal; a sensor substrate for mounting the image sensor; and a circuit board that is provided with the plurality of light sources on a same mounting surface and that is arranged on the sensor substrate on one side in the longitudinal direction of the plurality of light guides, wherein the sensor substrate includes a connection hole on one side in the longitudinal direction of the sensor substrate, and the circuit board is connected to the sensor substrate by connecting a connecting portion including a plurality of external connection pads to the connection hole.

13 Claims, 11 Drawing Sheets

(51) Int. Cl.
*G01N 21/86* (2006.01)
*G07D 7/20* (2016.01)
*G01N 21/88* (2006.01)
*G01N 21/89* (2006.01)
*G01J 3/02* (2006.01)
*G01J 3/10* (2006.01)

(52) U.S. Cl.
CPC ........... *G01J 3/0208* (2013.01); *G01J 3/0216* (2013.01); *G01J 3/0291* (2013.01); *G01J 3/10* (2013.01); *G01N 2021/8663* (2013.01)

(56) References Cited

U.S. PATENT DOCUMENTS

| | | | | |
|---|---|---|---|---|
| 2010/0303333 A1* | 12/2010 | Nireki | ...................... | G07F 7/04 382/135 |
| 2010/0322503 A1* | 12/2010 | Manabe | .................. | G07D 7/12 382/135 |
| 2010/0329507 A1* | 12/2010 | Manabe | ................. | G07D 7/122 382/100 |
| 2012/0207431 A1* | 8/2012 | Nakai | ................... | G02B 6/0006 385/31 |
| 2012/0250111 A1 | 10/2012 | Hozono | | |
| 2012/0318961 A1 | 12/2012 | Sawada | | |
| 2013/0038912 A1* | 2/2013 | Horiguchi | .......... | H04N 1/02855 358/474 |
| 2013/0265617 A1* | 10/2013 | Murakami | ........... | G02B 6/0001 358/448 |

FOREIGN PATENT DOCUMENTS

| | | |
|---|---|---|
| JP | 2009094935 A | 4/2009 |
| JP | 2010283436 A | 12/2010 |
| JP | 2012074857 A | 4/2012 |
| JP | 2012212069 A | 11/2012 |
| JP | 2012253747 A | 12/2012 |
| JP | 2013078102 A | 4/2013 |

* cited by examiner

IMAGE SENSOR UNIT, IMAGE READING APPARATUS, AND PAPER SHEET DISTINGUISHING APPARATUS

CROSS-REFERENCE TO RELATED APPLICATIONS

This application is based upon and claims the benefit of priority of the prior Japanese Patent Application No. 2013-219626, filed on Oct. 22, 2013, and the prior Japanese Patent Application No. 2014-208144, filed on Oct. 9, 2014, the entire contents of which are incorporated herein by reference.

BACKGROUND OF THE INVENTION

1. Field of the Invention

The present invention relates to an image sensor unit, an image reading apparatus, and a paper sheet distinguishing apparatus.

2. Description of the Related Art

In general, an image reading apparatus including an image sensor unit is used to read an image. An image sensor unit disclosed in Patent Document 1 includes light emitting units each arranged to face incident surfaces in a longitudinal direction of a plurality of light guides. Each light emitting unit includes an LED chip arranged to face the incident surface and a plurality of lead wires connected to a plate by soldering or the like.

Patent Document 1

Japanese Laid-open Patent Publication No. 2005-198106

To assemble the image sensor unit of the above-mentioned Patent Document 1, the lead wires need to be soldered after inserting the lead wires into vies formed on the plate, for each light emitting unit, Therefore, the number of light emitting units arranged to face the incident surfaces of the light guides increases with an increase in the number of light guides. Therefore, there is a problem that the number of processes for the insertion into the vias increases, and the work is troublesome. Furthermore, to insert the lead wires of a plurality of light emitting units into a plurality of vias of the plate, the lead wires of the plurality of light emitting units need to be aligned with the vias of the plate, and the work is troublesome.

SUMMARY OF THE INVENTION

The present invention has been made in view of the above-mentioned problems, and an object of the present invention is to provide an image sensor unit and the like that can be easily assembled.

The present invention provides an image sensor unit including: a plurality of light sources each including a light emitting element a plurality of light guides that are arranged in parallel to face incident surfaces on one side in a longitudinal direction for each of the plurality of light sources and that guide light from the plurality of light sources to an illuminated body; an image sensor that converts light from the illuminated body to an electric signal; a sensor substrate for mounting the image sensor; and a circuit board that is provided with the plurality of light sources on a same mounting surface and that is arranged on the sensor substrate on one side in the longitudinal direction of the plurality of light guides, wherein the sensor substrate includes a connection portion on one side in the longitudinal direction of the sensor substrate, and the circuit board is connected to the sensor substrate by connecting a connecting portion including a plurality of external connection pads to the connection portion.

The present invention provides an image reading apparatus including: the above-mentioned image sensor unit; and a transfer portion that relatively transfers the image sensor unit and the illuminated body.

The present invention provides a paper sheet distinguishing apparatus including: the above-mentioned image sensor unit; a transfer portion that transfers a paper sheet as the illuminated body; a storage portion that stores reference data as a reference for distinguishing the paper sheet; and a comparison portion that compares image information read by the image sensor unit and the reference data stored in the storage portion to distinguish the paper sheet.

DETAILED DESCRIPTION OF THE PREFERRED EMBODIMENTS

Hereinafter, preferred embodiments of an image sensor unit and an image reading apparatus according to the present invention will, be described with reference to the drawings. In the following description, three-dimensional directions will be indicated by X, Y, and Z arrows. The X direction denotes a main-scan direction, the Y direction denotes a sub scan direction perpendicular to the main-scan direction, and the Z direction denotes a perpendicular direction (vertical direction).

(First Embodiment)

An image reading apparatus 100 according to the present embodiment functions as a paper sheet distinguishing apparatus that authenticates a paper sheet, such as a bill and a security.

Figure 1:
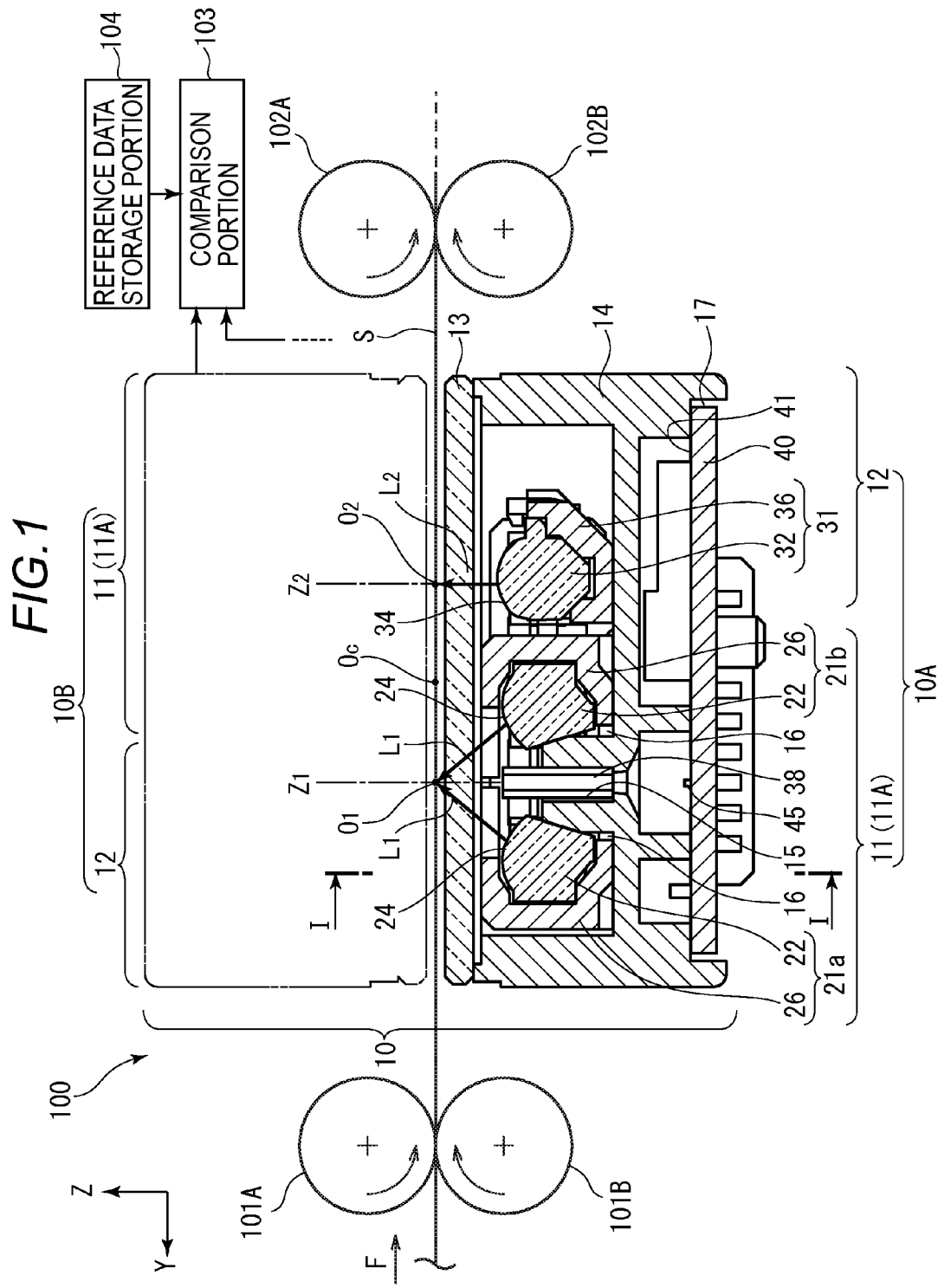
FIG. 1 is a sectional view showing a configuration of essential parts of an image reading apparatus of a first embodiment.

FIG. 1 shows a configuration of essential parts of the image reading apparatus 100 including an image sensor unit portion 10 according to the present embodiment. First, the entire configuration will be schematically described. In the present embodiment, a typical example of an, illuminated body is a bill S. However, the present invention can also be applied to objects other than the bill S.

At predetermined positions in the image reading apparatus 100, a pair of conveyor rollers 101A and 101B and a pair of conveyor rollers 102A and 102B as transfer portions for conveying the bill S held therebetween are disposed at predetermined intervals in a conveyance direction F of the bill S. The conveyor rollers 101A, 101B, 102A, and 102B are designed to be rotated by a driving mechanism to transfer the bill S relative to the image sensor unit portion 10 at a predetermined conveyance speed in the conveyance direction F.

The image sensor unit portion 10 is disposed between the pair of conveyor rollers 101A and 101B and the pair of conveyor rollers 102A and 102B to provide a gap that forms a conveyance path through which the bill S can pass and reads an image on the bill S conveyed. The image sensor unit portion 10 includes a lower image sensor unit 10A that serves as a first image sensor unit located below the conveyance path for the bill S and an upper image sensor unit 10B that serves as a second image sensor unit, located above the conveyance path for the bill In the present embodiment, the lower image sensor unit 10A and the upper image sensor unit 10B have the same configuration and are disposed symmetrically about a center line Oc shown in FIG. 1. Each of the lower image sensor unit 10A and the upper image sensor unit 10B includes an image reading portion 11 for reading an image that includes a reflection reading illumination portion 11A that emits light for reflection reading (reflection reading light) to the bill S and a transmission reading illumination portion 12 that emits light for transmission reading (transmission reading light) to the bill S. The image reading portion 11 (reflection reading illumination portion 11A) and the transmission reading illumination portion 12 allow reading of image information based on the reflected light, from the bill S and reading of image information based on the transmitted light. The transmission reading illumination portion 12 of the upper image sensor unit 10B is disposed in a position corresponding to the image reading portion 11 of the lower image sensor unit 10A. The image reading portion 11 of the upper image sensor unit 10B is disposed in a position corresponding to the transmission reading illumination portion 12 of the lower image sensor unit 10A. Thus, in the present embodiment, the lower image sensor unit 10A and the upper image sensor unit 10B can read both sides of the bill S in one conveyance.

A comparison portion 103 acquires image information read by the lower image sensor unit 10A and the upper image sensor unit 10B. The comparison portion 103 also reads reference data stored in a storage portion 104 and compares the reference data with the acquired image information to distinguish authenticity of the bill S.

Figure 2:
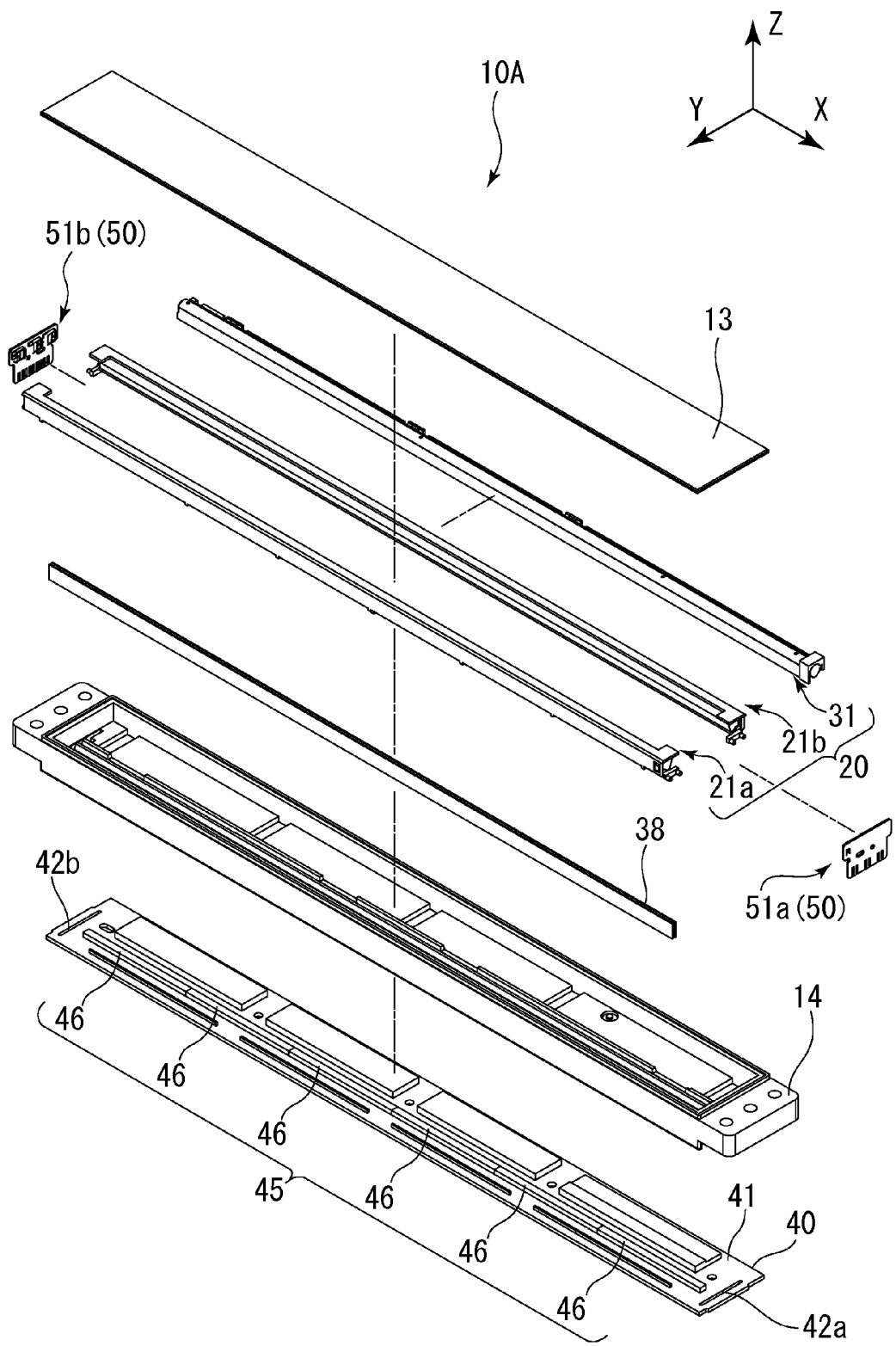
FIG. 2 is an exploded perspective view of a lower image sensor unit.
Figure 3:
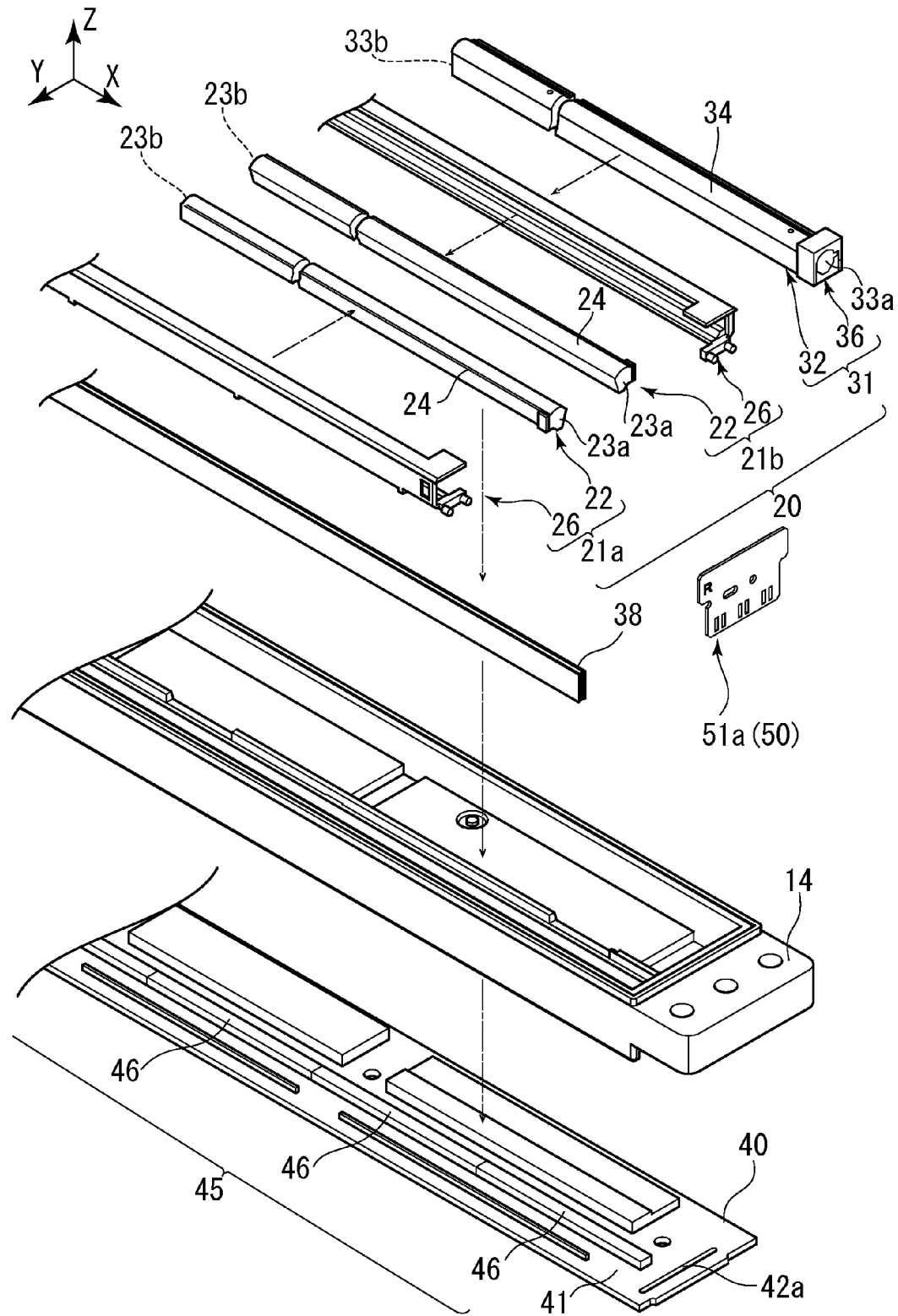
FIG. 3 is an enlarged exploded perspective view of the lower image sensor unit.

Next, configurations of the lower image sensor unit 10A and the upper image sensor unit 10B will be described. Since the lower: image sensor unit 10A and the upper image sensor unit 10B have the same configuration, the lower image sensor unit 10A will be particularly described here. FIG. 2 is an exploded perspective view of the lower image sensor unit 10A. FIG. 3 is an enlarged perspective view of one side in the longitudinal direction of the lower image sensor unit 10A shown in FIG. 2. The lower image sensor unit 10A has a generally rectangular shape, the longitudinal direction being aligned with the main-scan direction. The sub-scan direction perpendicular to the main-scan direction being aligned with the conveyance direction F of the bill S.

The lower image sensor unit 10A includes a cover glass 13, a frame 14, a light guide portion 20, a light condenser 38, a sensor substrate 40, an image sensor 45, a light source portion 50, and the like. Among the constituent members, the light guide portion 20 and the light source portion 50 function as an illumination apparatus. Among the above-mentioned constituent members, the cover glass 13, the frame 14, the light guide portion 20, the sensor substrate 40, and the image sensor 45 are formed in lengths according to a width dimension in the main-scan direction of the bill S to be read.

The cover glass 13 prevents dust from entering the frame 14. The cover glass 13 has a substantially plate shape, and for example, a double-sided tape or the like is used to fix the cover glass 13 so as to cover the frame 14 from above. The cover glass 13 is not limited to glass, and for example, a transparent resin material, such as an acrylic resin and polycarbonate, can be applied.

The frame 14 is a housing member that houses the constituent members of the lower image sensor unit 10A. The frame 14 is substantially rectangular solid. that is long in the main-scan direction and is formed to be able to position and support the constituent members inside. As shown in FIG. 1, a light condenser housing portion 15 that houses a light condenser 38 is formed in the main-scan direction, at substantially the center of the frame 14. Light guide housing portions 16 that house the light guide portion 20 are formed on the frame 14, on both sides across the light condenser housing portion 15. On a lower surface of the frame 14, a substrate housing portion 17 for arranging the sensor substrate 40 is formed in a concave shape from the outside of the frame 14 throughout the main-scan direction. The frame 14 can be made of a resin material such as polycarbonate.

The light guide portion 20 includes three light guide portions, a first reflection reading light guide portion 21a, a second reflection reading light guide portion 21b, and a transmission reading light guide portion 31.

The first reflection reading light guide portion 21a and the second reflection reading light guide portion 21b have substantially the same configuration and are disposed line-symmetrically about an optical axis $Z_1$ of the light condenser 38 shown in FIG. 1, and the first reflection reading light guide portion 21a will be described here.

As shown in FIG. 3, the first reflection reading light guide portion 21a includes a light guide 22 and a light guide holding member 26. The light guide 22 emits light from the light source portion 50 to the bill S as reflection reading light. The light guide 22 is formed by, for example, an acrylic transparent resin material and is formed in a rod shape that is long in the main -scan direction. The light guide 22 includes an incident surface 23a formed at an end on one side in he longitudinal direction and includes an incident surface 23b at an end on the other side. The incident surfaces 23a and 23b are orthogonal to the main-scan direction, and the light from the light source portion 50 enters.

The light guide 22 also includes, on a surface facing the bill S, an emission surface 24 for emitting the light incident on the light guide 22 toward the bill S. In the light guide 22, surfaces in the main-scan direction other than the emission surface 24 function as reflection surfaces for reflecting the light entered from the incident surfaces 23a and 23b and propagating the light in the longitudinal direction of the light guide 22.

The light guide holding member 26 holds the light guide 22. The light guide holding member 26 is formed in substantially the same length as the light guide 22 in the main-scan direction. As shown in FIG. 1, the light guide holding member 26 has a substantially C-shaped cross section, and the side on which the light condenser 38 is arranged is open.

The light guide holding member 26 covers a part of the emission surface 24 of the light guide 22 from above to control the direction of the light emitted to the bill S. An inner surface of the light guide holding member 26 functions as a reflection surface for reflecting the light incident on the light guide 22 toward the side of the emission surface 24 of the light guide 22.

Figure 4:
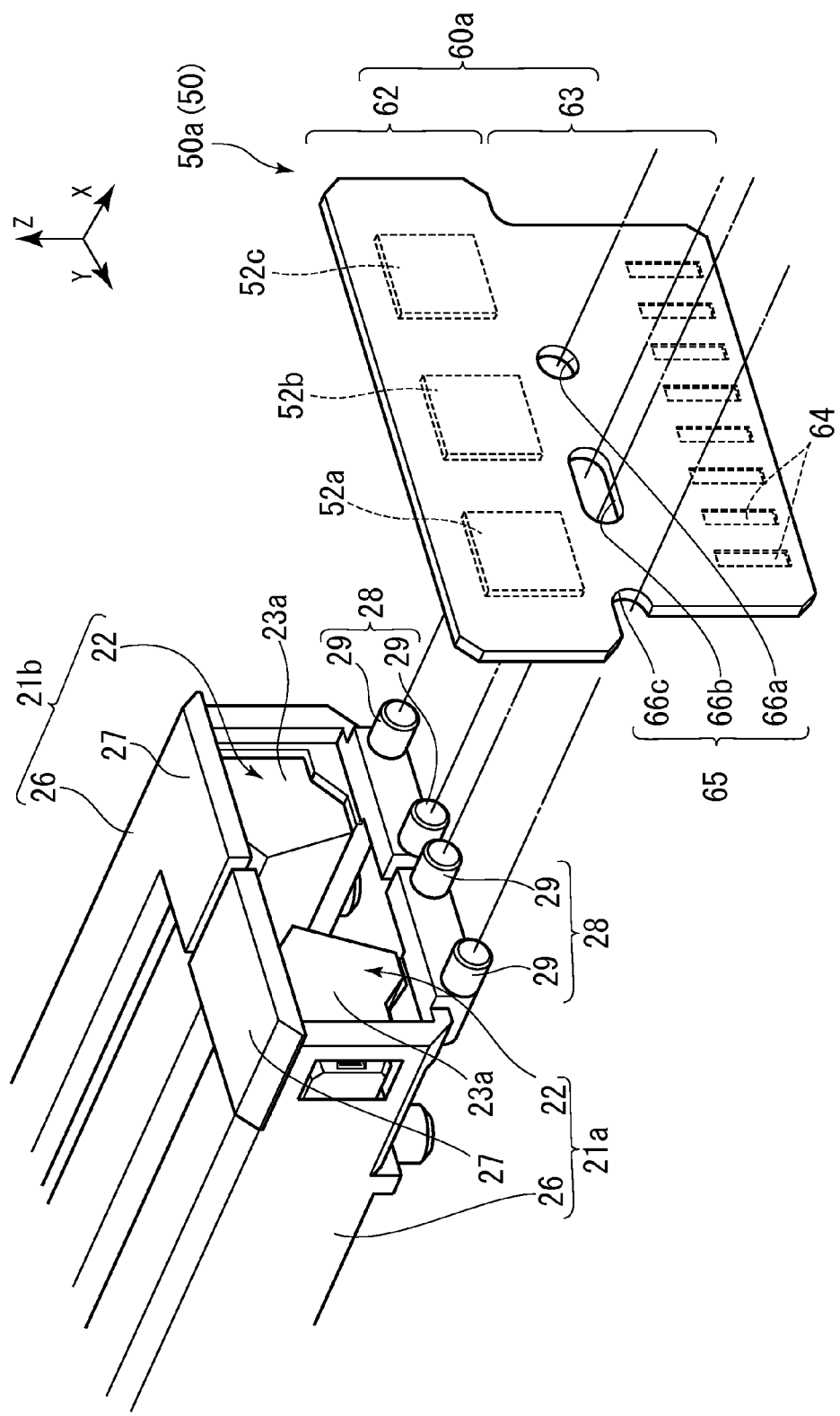
FIG. 4 is a perspective view showing a periphery of an end on one side in to longitudinal direction of a reflection reading light guide portion.

FIG. 4 is a perspective view showing a periphery of an end on one he in the longitudinal direction of the first reflection reading light guide portion 21a and the second reflection reading light guide portion 21b, As shown in FIG. 4, a plate-like eaves portion is integrally formed on the upper side at the end on one side in the longitudinal direction of the light guide holding member 26, and an alignment portion 28 is integrally formed on the lower side. The eaves portion 27 blocks and prevents the light from the light source portion 50 from leaking from between the incident surface 23a of the light guide 22 and the light source portion 50. The alignment portion 28 is a projection protruding toward the light source portion 50, and for example, a plurality of (two) cylindrical projections 29 are formed. The alignment portion 28 is engaged with an aligning portion 65 of a first circuit board 60a described later to position the light guide 22 and the light source portion 50 through the light guide holding member 26.

The eaves portion 27 and the alignment portion 28 are similarly formed at an end on the other side in the longitudinal direction of the light guide holding member 26.

As shown in FIG. 3, the transmission reading light guide portion 31 includes a light, guide 32 and a light guide holding member 36. The light guide 32 emits the light from the light source portion 50 to the bill S as transmission reading light. The light guide 32 is formed by, for example, an acrylic transparent resin material and is formed in a rod shape that is long in the main-scan direction. In the light guide 32, an incident surface 33a is formed at an end on one side in the longitudinal direction, and an incident surface 33b is formed at an end on the other side. The incident surfaces 33a and 33b are orthogonal to the main-scan direction, and the light from the light source portion 50 enters In the light guide 32, an emission surface 34 for emitting the light incident on the light guide 32 toward the bill S is formed on a surface facing the bill S. In the light guide 32, surfaces in the main-scan direction other than the emission surface 34 function as reflection surfaces for reflecting the light entered from the incident surfaces 33a and 33b and propagating the light in the longitudinal direction in the light guide 32.

The light guide holding member 36 holds the light guide 32. The light guide holding member 36 is formed in substantially the same length as the light guide 32 in the main-scan direction. As shown in FIG. 1, the light guide holding member 36 has a substantially C-shaped cross section, and the upper side is open.

The light guide 22 of the first reflection reading light guide portion 21a, the light guide 22 of the second reflection reading light guide portion 21b, and the light guide 32 of the transmission reading light guide portion 31 are arranged in parallel in the sub scan direction in the frame 14.

The light condenser 38 is an optical member that focuses the reflected light from the bill S and the transmitted light from the bill S on the image sensor 45. The light condenser 38 can be for example, a rod-lens array with a plurality of image forming elements (rod lenses) of an erect equal magnification image forming type linearly arranged in the main-scan direction. The configuration of the light condenser 38 is not limited to the above-mentioned configuration as long as an image can be formed on the image sensor 45. The light condenser 38 can be an optical member with various conventionally well-known light condensing functions, such as various micro-lens arrays.

The sensor substrate 40 is formed in a planar shape that is long in the main-scan direction. A mounting surface 41 of the sensor substrate 40 is orthogonal to the vertical direction. A drive circuit and the like for emitting light from the light source portion 50 or driving the image sensor 45 are mounted on the mounting surface 41 of the sensor substrate 40. A connection hole 42a as a connection portion for inserting the first circuit board 60a is formed at an end on one side in the longitudinal direction of the sensor substrate 40, and a connection hole 42b as a connection portion for inserting a second circuit board 60b is formed at an end on the other side. The connection holes 42a and 42b have an elongated shape that is long in the sub-scan direction.

The image sensor 45 is mounted on the sensor substrate 40 and arranged below the condenser 38. The image sensor 45 includes a predetermined number of image sensor ICs 46 that are configured by a plurality of photoelectric conversion elements corresponding to the resolution of reading by the lower side image sensor unit 10A and that are linearly arranged on the mounting surface 41 in the main-scan direction. The image sensor 45 receives the reflected light and the transmitted light from the bill S focused by the light condenser 38 and converts the light to an electric signal. The image sensor 45 is not limited to the above-mentioned configuration as long as the reflected light and the transmitted light from the bill S can be converted to an electric signal. The image sensor ICs 46 can be various conventionally well-known image sensor ICs.

The light source portion 50 generates light to emit the light to the bill S through the light guide portion 20. The light source portion 50 includes a first light source portion 51a arranged at an end on one side in the longitudinal direction of the light guide portion 20 and a second light source portion 51b arranged at an end on the other side.

Figure 5A:
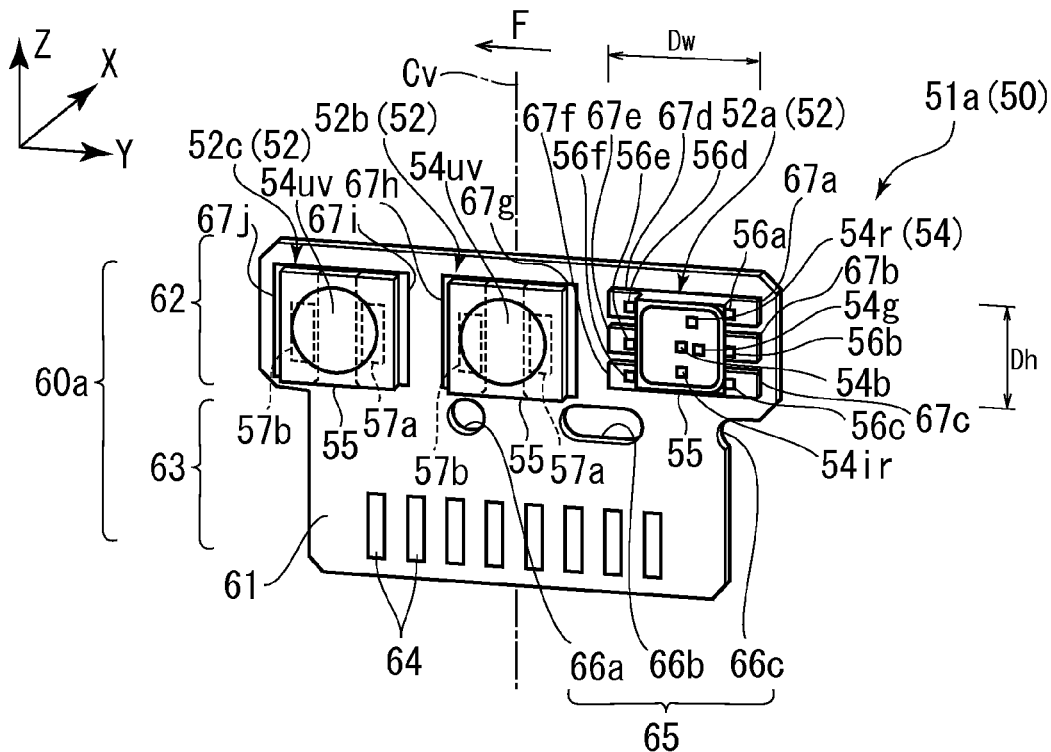
FIG. 5A is a perspective view showing a configuration of a first light source portion of the first embodiment.

FIG. 5A is a perspective view showing a configuration of the first light source portion 51a. The first light source portion 51a includes a plurality of light sources 52 (52a, 52b, and 52c) mounted on a same mounting surface 61 of the first circuit board 60a. The light sources 52 can be so-called top-view surface-mount LED packages, in which LED chips 54 as light emitting elements are mounted on the surface. The surface-mount LED packages are widely used, and the costs can be reduced by using the LED packages in the lower side image sensor unit 10A.

The plurality of light sources 52 (52a, 52b, and 52c) are mounted in parallel in the sub-scan direction (conveyance direction F), with the light emitting surfaces facing the main-scan direction.

In the first light source portion 51a, the light source mounted on the upstream in the conveyance direction F is a first reflection reading light source 52a arranged to face the incident surface 23a of the light guide 22 of the first reflection reading light guide portion 21a. The first reflection reading light source 52a is arranged in a state that a plurality of (for example, four) LED chips 54r, 54g, 54b, and 54ir are sealed by a transparent resin. The LED chips 54r, 54g, and 54b emit visible light with emission wavelengths of red, green, and blue (hereinafter, also called RGB), respectively. The LED chip 54ir emits light with an emission wavelength of infrared light (hereinafter, also called IR). The reason that the light with an emission wavelength of invisible light, such as infrared light, is emitted is to read an image on the bill S printed by an invisible ink.

The first reflection reading light source 52a includes a plurality of terminals 56a to 56f as electrodes extending from a rectangular package body 55. The terminals 56a to 56c extend from a side surface on one side in the sub-scan direction of the package body 55, and the terminals 56d to 56f extend from a side surface on the other side in the sub-scan direction of the package body 55.

In the first light source portion 51a, the light source mounted at the center is a second reflection reading light source 52b arranged to face the incident surface 23a of the light guide 22 of the second reflection reading light guide portion 21b. The second reflection reading light source 52b is arranged in a state that an LTD chip 54uv is sealed by a transparent resin. The LED chip 54uv emits light with an emission wavelength of ultraviolet light (hereinafter, also called UV).

The second reflection reading light source 52b includes electrodes 57a and 57b formed on the back surface of the rectangular package body 55. The electrodes 57a and 57b are separately positioned in the sub-scan direction.

In the first light source portion 51a, the light source mounted on the downstream in the conveyance direction F is a transmission reading light source 52c arranged to face the incident surface 33a of the light guide 32 of the transmission reading light guide portion 31. The transmission reading light source 52c is arranged in a stare that an LED chip 54uv is sealed by a transparent resin.

The transmission reading light source 52c includes electrodes 57a and 57b formed on the back surface of the rectangular package body 55. The electrodes 57a and. 57b are separately positioned in the sub-scan direction.

The first circuit board 60a is formed in a planar shape. The upper side is a mounting portion 62 provided with the plurality of light sources 52, and the lower side is a connecting portion 63 connected to the connection hole 42a of the above-mentioned sensor substrate 40.

A plurality of light source connection pads 67a to 67j are exposed and formed on the mounting surface 61 of the mounting portion 62. The terminals 56a to 56f of the first reflection reading light source 52a are soldered and connected to the light source connection pads 67a to 67f, respectively, and the first reflection reading light source 52a is mounted on a predetermined position of the mounting portion 62. The light source connection pads 67a to 67f are formed in a size exceeding the terminals 56a to 56f in the sub-scan direction so that the terminals 56a to 56f extending in the sub-scan direction can be easily soldered to the light source connection pads 67a to 67f. More specifically, the light source connection pads 67a to 67f are formed so that a length Dh in the vertical direction (direction orthogonal to width direction) is shorter than a length Dw in the width direction (sub-scan direction) in the outer shape of the light source connection pads 67a to 67f combined.

The terminals 57a and 57b of the second reflection reading light source 52b are soldered and connected to the light source connection pads 67g and 67h, respectively, and the second reflection reading light, source 52b is mounted on a predetermined position of the mounting portion 62. The light source connection pads 67g and 67h are formed in a size exceeding the package body 55 in the sub-scan direction so that the terminals 57a and 57b separated in the sub-scan direction can be easily soldered to the light, source connection pads 67g and 67h. More specifically, the light source connection pads 67g and 67h are formed so that the length in the vertical direction is shorter than the length in the width direction in the outer shape of the light source connection pads 67g and 67h combined.

The terminals 57a and 57b of the transmission reading light sources 52c are soldered and connected to the light source connection pads 67i and 67j, respectively, and the transmission reading light source 52c is mounted on a predetermined position of the mounting portion 62. As in the light source connection pads 67g and 67h, the light source connection pads 67i and 67j are formed so that the length in the vertical direction is shorter than the length in the width direction in the outer shape of the light source connection pads 67i and 67j combined, In this way, the light source connection pads 67a to 67f, 67g and 67h, and 67i and 67j are formed so that the length in the vertical direction is shorter than the length in the width direction in the outer shapes of the light source connection pads 67a to 67f, 67g and 67h, and 67i and 67j combined, respectively. Therefore, the length in the vertical direction of the mounting portion 62 can be reduced.

Meanwhile, a plurality of (for example, eight) external connection pads 64 for electrical connection with the sensor substrate 40 are formed on the connecting portion 63 at predetermined intervals in he conveyance direction F. A circuit pattern not shown is formed on the connecting portion 63, and the light source connection pads 67a to 67j and the external connection pad 64 are electrically connected. An aligning portion 65 is also formed on the connecting portion 630 The aligning portion 65 includes: insertion holes 66a and 66b for inserting the projections 29 of the light guide holding member 26; and a cut-out portion 66c.

Figure 5B:
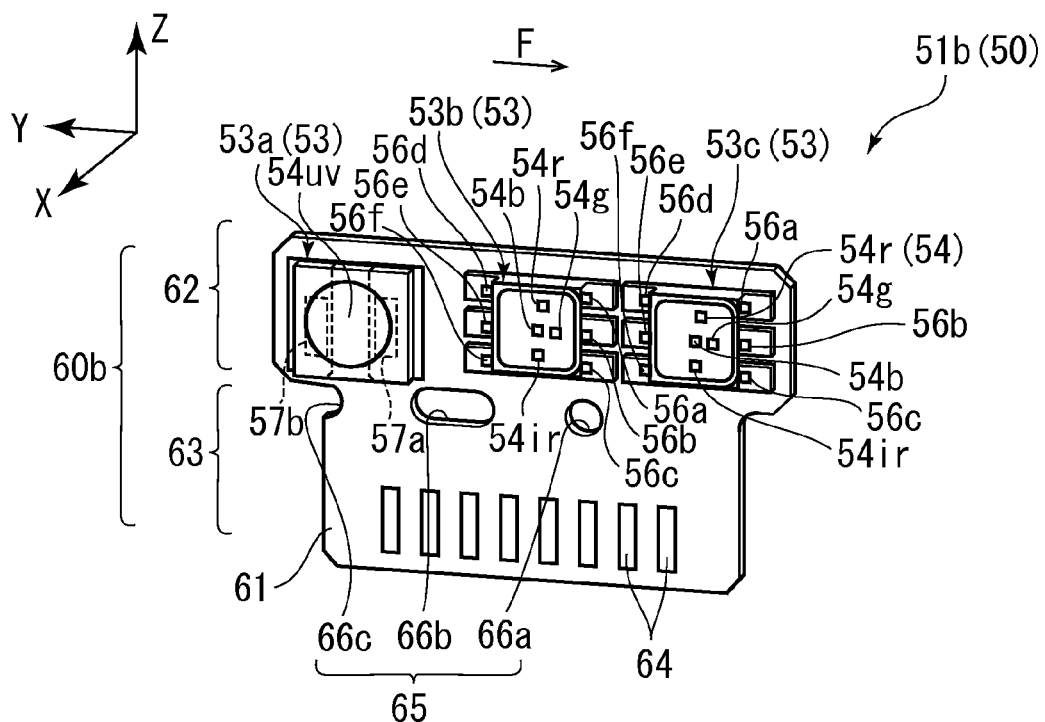
FIG. 5B is a perspective view showing a configuration of a second light source portion of the first embodiment.

Meanwhile, FIG. 5B is a perspective view showing a configuration of the second light source portion 51b. The second light source portion 51b includes a plurality of light sources 53 (53a, 53b, and 53c) mounted on the same mounting surface 61 of the second circuit board 60b. in the second light source portion 51b, as in the first light source portion 51a, a plurality of light sources (53a, 53b, and 53c) are mounted in parallel in the sub-scan direction (conveyance direction F), with the light emitting surfaces facing the main-scan direction.

In the second light source portion 51b, the light source mounted on the upstream in the conveyance direction F is a first reflection reading light source 53a arranged to face the incident surface 23b of the light guide 22 of the first reflection reading light guide portion 21a. The first reflection reading light, source 53a is arranged in a state that an LED chip 54uv is sealed by a transparent resin.

In the second light source portion 51b, the light source mounted at the center is a second reflection reading light source 53b arranged to face the incident surface 23b of the light guide 22 of the second reflection reading light guide portion 21b. The second reflection reading light source 53b is arranged in a state that a plurality of (for example, four) LED chips 54r, 54g, 54b, and 54ir are sealed by a transparent resin.

In the second light source portion 51b, the light source mounted on the downstream in the conveyance direction F is a transmission reading light source 53c arranged to face the incident surface 33b of the light guide 32 of the transmission reading light guide portion 31. The transmission reading light source 53c is arranged in as state that a plurality of (for example, four) LED chips 54r, 54g, 54b, and 54ir are sealed by a transparent resin.

The light sources of the second light source portion 51b includes electrodes as in the light sources of the first light source portion 51a. The same reference numerals as in the first light source portion 51a are designated here, The second circuit board 60b is formed in a planar shape. The upper side is a mounting portion 62 provided with the plurality of light sources 52, and the lower side is a connecting portion 63 connected to the connection hole 42b of the sensor substrate 40. As in the first light source portion 51a, light source connection pads are also formed on the mounting surface 61 of the mounting portion 62. More specifically, as in the first light source portion 51a, the second circuit board 60b is also formed, so that the length in the vertical direction is shorter than the length in the width direction in the outer shape of the light source connection pads combined. Therefore, the length in the vertical direction of the mounting portion 62 can be reduced.

The outer shape of the second circuit board 60b is mirror-symmetric with respect to the outer shape of the first circuit board. 60a. More specifically, the outer shape of the second circuit board 60b is line-symmetric about a center line Cv of the first circuit board 60a shown in FIG. 5A. The same components are designated with the same reference numerals, and the description will not be repeated.

Therefore, the first reflection reading light source 52a and the first reflection reading light source 53a arranged on both ends in the longitudinal direction of the first reflection reading light guide portion 21a cause red, green, blue, infrared, and ultraviolet lights to enter the first reflection reading light guide portion 21a through the incident surfaces 23a and 23b.

Similarly, the second reflection reading light source 52b and the second reflection reading light source 53b arranged on both ends in the longitudinal direction of the second reflection reading light guide portion 21b cause red, green, blue, infrared, and ultraviolet lights to enter the second reflection reading light guide portion 21b through the incident surfaces 23a and 23b.

Similarly, the transmission reading light source 52c and the transmission reading light source 53c arranged on both ends in the longitudinal direction of the transmission reading light guide portion 31 cause red, green, blue, infrared, and ultraviolet lights to enter the transmission reading light guide portion 31 through the incident surfaces 33a and 33b.

Next, basic operation of the image reading portion 11 configured as described above will be described. The image reading portion 11 successively activates the LED chips 54r, 54g, 54b, 54ir, and 54uv of the first reflection reading light sources 52a and 53a and the second reflection reading light sources 52b and 53b, with respect to the bill S conveyed by the conveyor rollers 101A, 101S, 102A, and 102B in the conveyance direction F at a predetermined conveyance speed. The light emitted from the first reflection reading light sources 52a and 53a and the second reflection reading light sources 52b and 53b enters the light guides 22 of the first reflection reading light guide portion 21a and the second reflection reading light guide portion 21b from the incident surfaces 23a and 23b. The incident light is emitted as reflection reading light from the emission surfaces 24 of the light guides 22 of the first reflection reading light guide portion 21a and the second reflection reading light guide portion 21b, toward a reading position $O_1$ of the bill S as representatively indicated by arrows $L_1$ in FIG. 1. The reflection reading light is linearly and uniformly illuminated on one of the surfaces (lower surface) of the bill S in the main-scan direction, from two directions across the light condenser 38.

The reflection reading light is reflected by the bill S, and the reflected light is focused on the image sensor 45 through the light condenser 38. The image sensor 45 converts the focused reflected light to an electric signal, and a signal processing unit not shown processes the electric signal.

In this way, one scan line of all, of the RGB, IR, and UV reflected lights is read, and the reading operation of one scan line in the main-scan direction of the bill S is completed. After the completion of the reading operation of one scan line, reading operation of the next scan line is performed in the same way, along with the movement of the bill S in the sub-scan direction. In this way, the reading operation of one scan line is repeated while conveying the bill S in the conveyance direction F, The entire surface of the bill S is successively scanned, and image information is read based on the reflected light.

The image reading portion 11 of the upper image sensor unit 10B performs the same operation for the other surface (upper surface).

Next, operation of the transmission reading illumination portion 12 configured as described above will be described. The transmission reading illumination portion 12 successively activates the LED chips 54r, 54g, 54b, 54ir, and 54uv of the transmission reading light sources 52c and 53c, with respect to the bill S conveyed by the conveyor rollers 101A, 101B, 102A, and 102B in the conveyance direction F at a predetermined conveyance speed. The light emitted from the transmission reading light sources 52c and 53c enters the transmission reading light guide portion 31 from the incident surfaces 33a and 33b. The incident light is emitted as transmission reading light from the emission surface 34 of the transmission reading light guide portion 31, toward a reading position $O_2$ of the bill S as representatively indicated by an arrow $L_2$ in FIG. 1. The transmission reading light is linearly and uniformly illuminated on one of the surfaces (lower surface) of the bill S in the main-scan direction.

The transmission reading light transmits through the bill S, and the transmitted light is focused on the image sensor 45 through the light condenser 38 of the upper image sensor unit 10B. The image sensor 45 of the upper image sensor unit 10B converts the focused transmitted light to an electric signal, and a signal processing unit not shown processes the electric signal.

In this way, one scan line of all of the RGB, IR, and UV transmitted lights is read, and the reading operation of one scan line in the main-scan direction of the bill S is completed. After the completion of the reading operation of one scan line, reading operation of the next scan line is performed in the same way, along with the movement of the bill S in the sub-scan direction. In this way, the reading operation of one scan line is repeated while conveying the bill S in the conveyance direction F. The entire surface of the bill S is successively scanned, and image information is read based on the transmitted light.

The transmission reading illumination portion 12 of the upper image sensor unit 10B performs the same operation for the other surface (upper surface).

Next, an assembly method of the image sensor unit portion 10 configured as described above will be described.

The lower image sensor unit 10A and the upper image sensor unit 10B have substantially the same configuration, and the lower image sensor unit 10A will be described here.

First, the constituent members of the lower image sensor unit 10A are prepared. In this case, the plurality of light sources 52 are mounted in advance on predetermined positions as shown in FIG. 5A and 5B in the first circuit board 60a and the second circuit board 60b. The image sensor 45, the drive circuit, and the like, are mounted in advance on predetermined positions in the sensor substrate 40.

Next, the light guide holding members 26 hold the light guides 22 to form the first reflection reading light guide portion 21a and the second reflection reading light guide portion 21b. Similarly, the light guide holding member 36 holds the light guide 32 to form the transmission reading light guide portion 31.

Next, as shown in FIG. 4, the first reflection reading light guide portion 21a and the second reflection reading light guide portion 21b is maintained to face each other. In this state, the alignment portions 28 formed on one side in the longitudinal direction of the light guide holding members 26 and the aligning portion 65 of the first circuit board 60a are engaged and positioned. Specifically, the projections 29 of the alignment portions 28 are inserted into the insertion holes 66a, 66b, and the cut-out portion 66c. Two projections 29 are inserted into the insertion hole 66b.

Therefore, the first reflection reading light source 52a accurately faces the incident surface 23a of the light guide 22 of the first reflection reading light guide portion 21a, and the second reflection reading light source 52b accurately faces the incident surface 23a of the light guide 22 of the second reflection reading light guide portion 21b.

Similarly, the alignment portions 28 formed on the other side in the longitudinal direction of the light guide holding members 26 and the aligning portion 65 of the second circuit board 60b are engaged and positioned.

Therefore, the first reflection reading light source 53a accurately faces the incident surface 23b of the first reflection reading light guide portion 21a, and the second reflection reading light source 53b accurately faces the incident surface 23b of the second reflection reading light guide portion 21b.

Next, the light condenser 38 is housed in the light condenser housing portion 15 from the upper side of the frame 14. Furthermore, the first reflection reading light, guide portion 21a and the second reflection reading light guide portion 21b including the positioned first circuit board 60a and second circuit board 60b are housed in the light guide housing portions 16 from the upper side of the frame 14. Similarly, the transmission reading light guide portion 31 is housed in the light guide housing portion 16 from the upper side of the frame 14. The cover glass 13 is fixed on the upper surface of the frame 14 to cover the upper side of the frame 14.

Next, the frame 14 is vertically inverted so that the cover glass 13 serves as a lower surface, and the vertically inverted sensor substrate 40 is housed in the substrate housing portion 17. In this case, the connecting portion 63 of the first circuit board 60a protruding from the frame 14 is inserted into the connection hole 42a formed on one side in the longitudinal direction of the sensor substrate 40. The connecting portion 63 of the second circuit board 60b protruding from the frame 14 is inserted into the connection hole 42b formed on the other side in the longitudinal direction of the sensor substrate 40. Therefore, the first circuit board 60a and the second circuit board 60b are connected to the ends in the longitudinal direction of the sensor substrate 40.

In this case, only one location needs to be aligned at each of the end on one side and the end on the other side in the longitudinal direction of the sensor substrate 40 to insert the first circuit board 60a and the second circuit board 60b, and the workability for housing the sensor substrate 40 in the frame 14 is improved. More specifically, unlike in the conventional technique, a plurality of lead wires do not have to be aligned and inserted into a plurality of visa at the same time, and the first circuit board 60a and the second circuit board 60b can be easily connected to the sensor substrate 40.

The external connection pads 64 of the first circuit board 60a and the second circuit board 60b exposed from the lower surface of the sensor substrate 40 are soldered to the sensor substrate 40 from the connection holes 42a and 42b. The sensor substrate 40 housed in the substrate housing portion 17 is fixed in the substrate housing portion 17 by, for example, heat caulking, and the lower image sensor unit 10A is manufactured.

Figure 6:
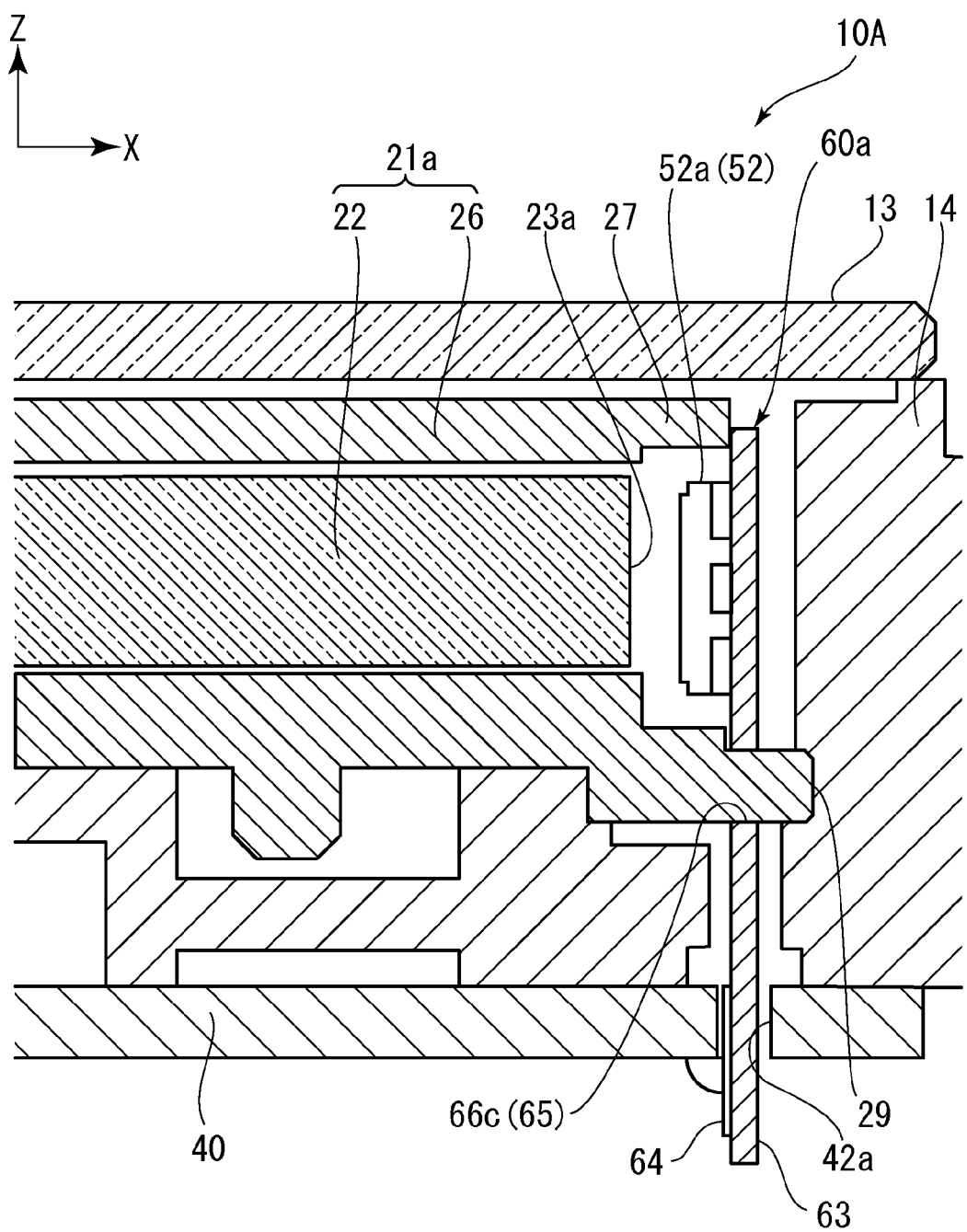
FIG. 6 is a sectional view of a part of the lower image sensor unit of the first embodiment.

FIG. 6 is a sectional view of one side in the longitudinal direction of the manufactured lower image sensor unit 10A and is equivalent to a sectional view of a I-I line shown in FIG. 1. As shown in FIG. 6, the projection 29 of the light guide holding member 26 is inserted into the cut-out portion 66c of the first circuit board 60a, and the light source 52 is housed in the frame 14 to face the incident surface 23a of the it guide 22.

In this way, the image sensor unit of the present embodiment includes the first circuit board 60a including the plurality of light sources 52a, 52b, and 52c mounted on the same mounting surface 61, and the first circuit board 60a is connected to the sensor substrate 40 on one side in the longitudinal direction of the plurality of light guides 22 and 32. Therefore, the plurality of light sources 52a, 52b, and 52c can be connected to the sensor substrate 40 through he first circuit board 60a just by aligning and connecting the first, circuit board 60a and the sensor substrate 40 at one location, and the image sensor unit can be easily manufactured.

The image sensor unit of the present embodiment also includes the second circuit, board 60b including the plurality of light sources 53a, 53b, and 53c mounted on the same mounting surface 61, and the second circuit board 60b is connected to the sensor substrate 40 on the other side in the longitudinal direction of the plurality of light guides 22 and 32 Therefore, as described above, the image sensor unit can be easily manufactured.

In the image sensor unit of the present embodiment, the plurality of light sources 52a, 52b, and 52c are arranged at the end on one side in the longitudinal direction of the light guides 22 and 32, and the plurality of light sources 53a, 53b, and 53c are arranged at the end on the other side. Therefore, compared to when a plurality of light sources are arranged only on one side, the plurality of light sources 52 can be arranged to face the incident surfaces 23a, 23b, 33a, and 33b without increasing the areas of the incident surfaces 23a and 23b of the light guide 22 and the incident surfaces 33a and 33b of the light guide 32.

(Second Embodiment)

In the first embodiment, the case of arranging the first reflection reading light guide portion 21a and the second reflection reading light guide portion 21b on both sides across the light condenser 38 has been described. In a second embodiment, a case of arranging just one reflection reading light guide portion 81 on one side of the light condenser 38 will be described.

Figure 7A:
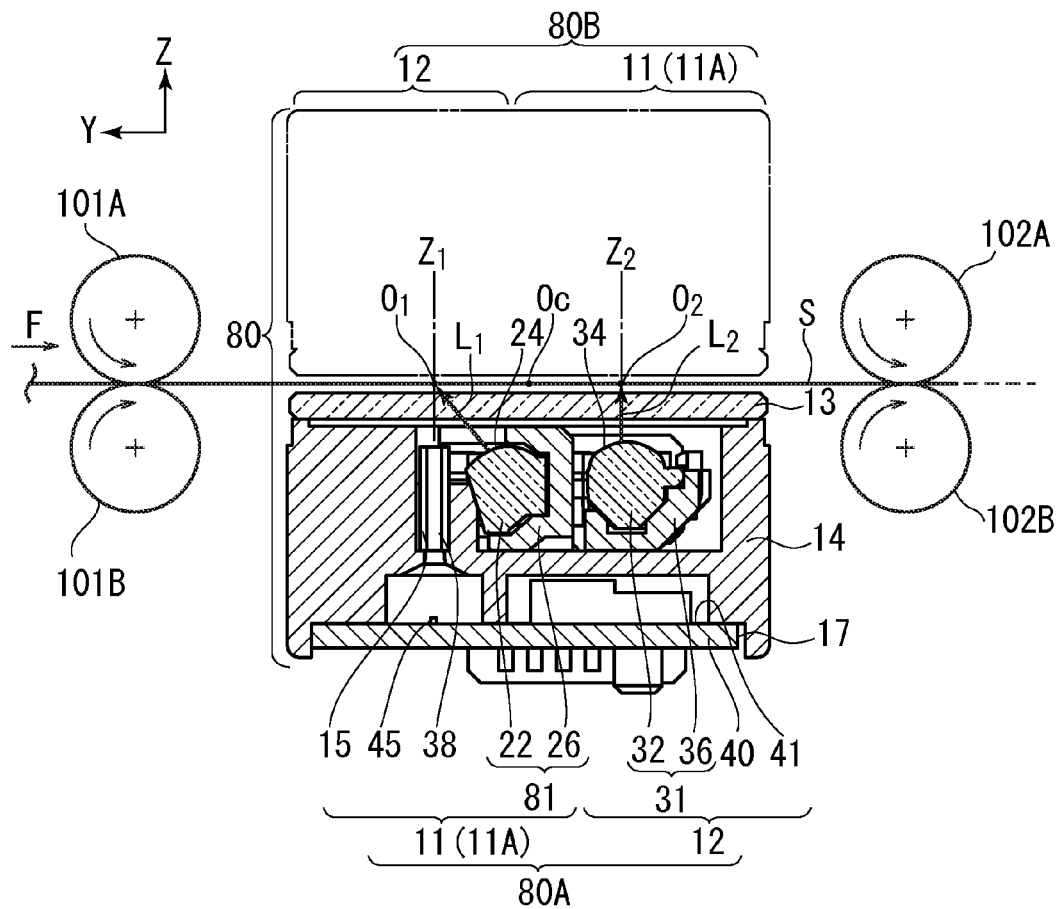
FIG. 7A is a sectional view of as lower image sensor unit of a second embodiment.

FIG. 7A is a sectional view showing a lower image sensor unit 80A of the second embodiment. The same components as in the first embodiment are designated with the same reference numerals, and the description will not be repeated. As shown in FIG. 7A, the lower image sensor unit 80A does not include the first reflection reading light guide portion 21a of the first embodiment and includes just one reflection reading light Guide portion 81. Therefore, the lower image sensor unit 80A includes two light guide portions, the reflection reading light guide portion 81 and the transmission reading light guide portion 31.

Figure 7B:
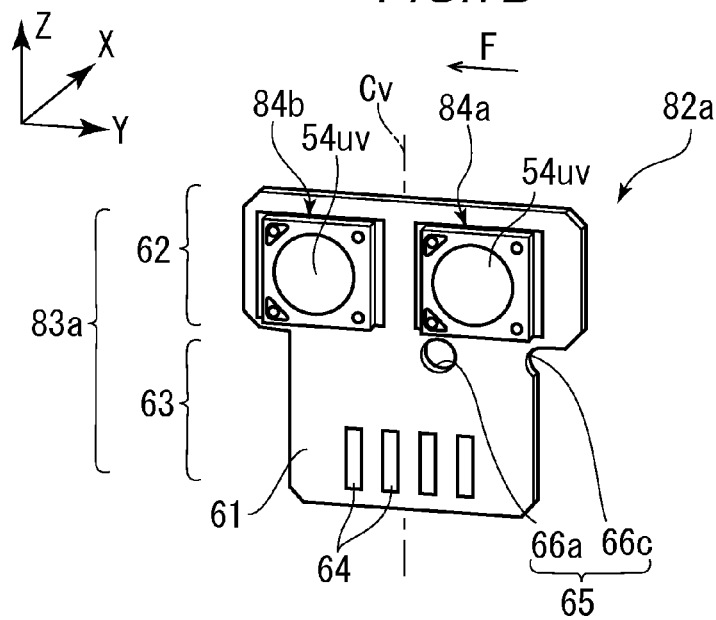
FIG. 7B is a perspective view showing a configuration of a first light source portion of the second embodiment.

FIG. 7B is a per view showing a light source portion 82a arranged at an end on one side in the longitudinal direction of the reflection reading light guide portion 81 and the transmission reading light guide portion 31 and mounted on a first circuit board 83a. The same components as in the first embodiment are designated with the same reference numerals, and the description will not be repeated, As shown in FIG. 7B, the first circuit board 83a includes a first light source 84a and a second light source 84b mounted in parallel on the same mounting surface 61. The first light source 84a faces the Incident surface 23a of the reflection reading light guide portion 81, and the second light source 84b faces the incident surface 33a of the transmission reading light guide portion 31.

According to the present embodiment, the plurality of light sources 84a and 84b can he connected to the sensor substrate 40 through the first circuit board 83a just by aligning and inserting the connecting portion 63 of the first circuit hoard 83a into the connection hole 42a of the sensor substrate 40, and the image sensor unit can be easily manufactured. Although not shown, a light source portion may also be arranged at an end on the other side in the longitudinal direction of the reflection reading light guide portion 81 and the transmission reading light guide portion 31. In this case, the light source portion has a configuration excluding the first light source 53a shown in FIG. 5B, and a second circuit board has a shape line-symmetric about the center line Cv of the first, circuit board 83.

(Third Embodiment)

In the first embodiment, the case of arranging the transmission reading light guide portion 31 to emit the transmission reading light to the bill S has been described. In a third embodiment, a case excluding the transmission reading light guide portion 31 to emit just the reflection reading light will be described.

Figure 8A:
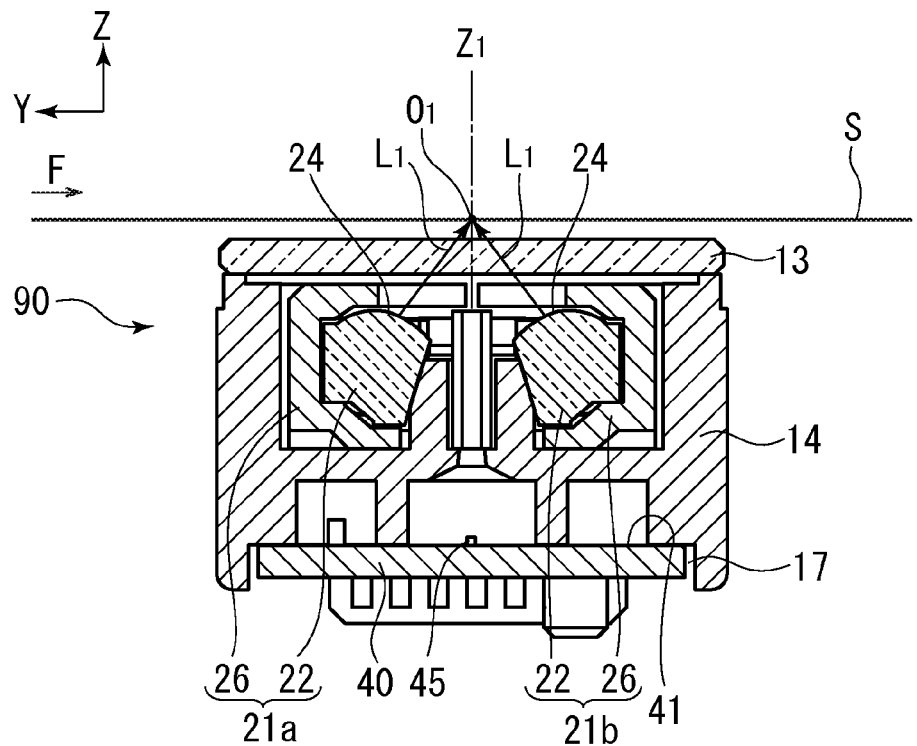
FIG. 8A is a sectional view of an image sensor unit of a third embodiment.

FIG. 8A is a sectional view showing an image sensor unit 90 of the third embodiment. There is no need to read the transmitted light here, and the upper image sensor unit is not arranged above the bill S. The same components as in the first embodiment are designated with the seine reference numerals, and the description will not be repeated. As shown in FIG. 8A, the image sensor unit 90 has a configuration excluding the transmission reading light guide portion 31 of the first embodiment. More specifically, the lower image sensor unit 90 includes two light guide portions, the first reflection reading light guide portion 21a and the second reflection reading light guide portion 21b.

Figure 8B:
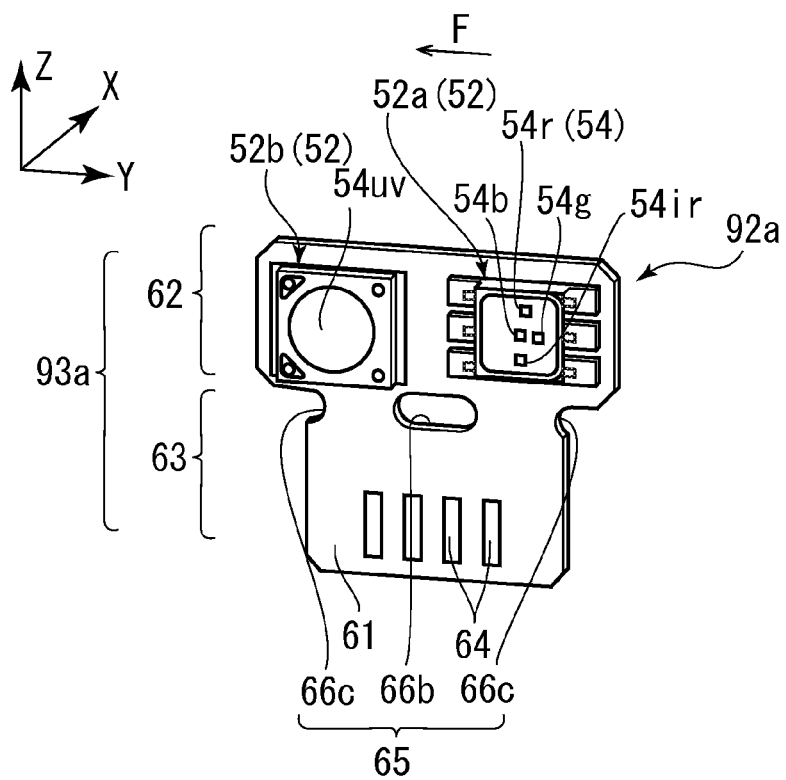
FIG. 8B is a perspective view showing a configuration of a first light source portion of the third embodiment.

FIG. 8B is a perspective view showing a light source portion 92a arranged at an end on one side in the longitudinal direction of the first reflection reading light guide portion 21a and the second reflection reading light guide portion 21b and mounted on a first circuit board 93a. The same components as in the first embodiment are designated with the same reference numerals, and the description will not be repeated. As shown in FIG. 8B, the first circuit board 93a includes the first light source 52a and the second light source 52b mounted in parallel on the same mounting surface 61. The first light source 52a faces the incident surface 23a of the first reflection reading light guide portion 21a, and the second light source 52b faces the incident surface 23a of the second reflection reading light guide portion 21b.

According to the present embodiment, the plurality of light sources 52a and 52b can be connected to the sensor substrate 40 through the first circuit board 93a lust by aligning and inserting the connecting portion 63 of the first circuit board 93a into the connection hole 42a n the sensor substrate 40, and the image sensor unit can be easily manufactured. Although not shown, a light source portion may also be arranged at an end on the other side in the longitudinal direction of the first reflection reading light guide portion 21a and the second reflection reading light guide portion 21b. In this case, the light source portion has a configuration excluding the third light source 53c shown in FIG. 5B, and a second circuit board has the same shape as the first circuit board 93a.

(Fourth Embodiment)

In the first embodiment, the case has been described in which the light source connection pads of the first circuit board 60a and the second circuit board 60b are formed so that the outer shape of the plurality of light source connection pads combined is short in the vertical direction. In the present embodiment, a case in which the outer shape of a plurality of light source connection pads combined is short in the width direction will be described.

Figure 9A:
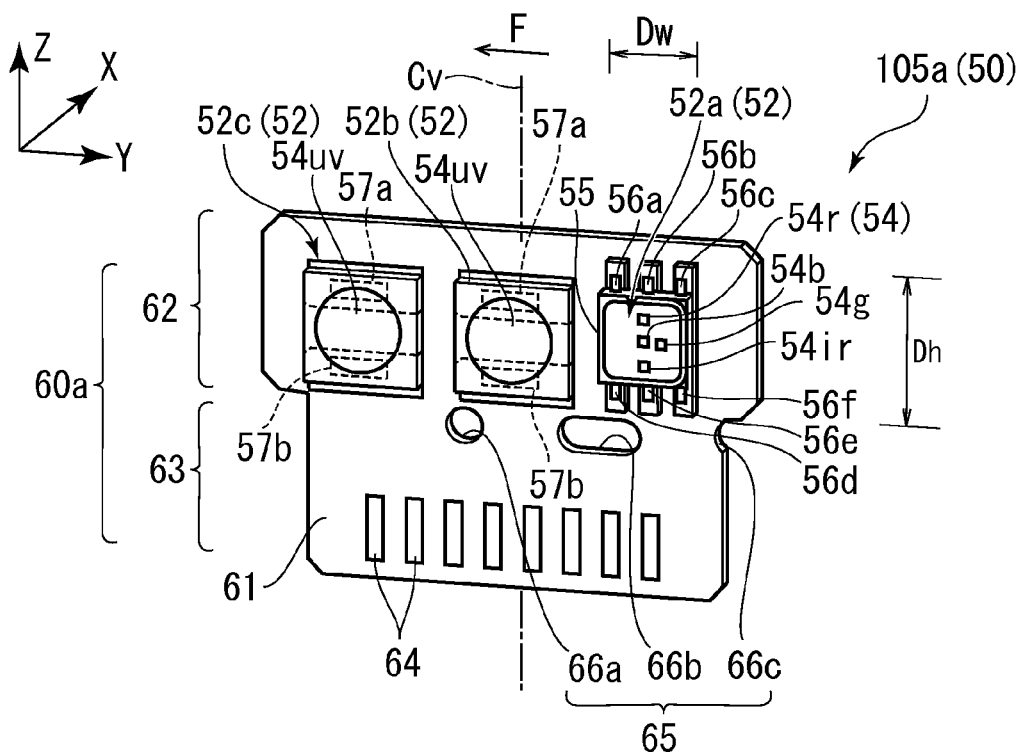
FIG. 9A is a perspective view showing a configuration of a first light source portion of a fourth embodiment.

FIG. 9A is a perspective view showing a configuration of a first light source portion 105a of the present embodiment. As shown in FIG. 9A, the first reflection reading light source 52a, the second reflection reading light source 52b, and the transmission reading light source 52c of the first light source portion 105a are rotated 90 degrees from the first embodiment and mounted on the mounting surface 61.

More specifically, the terminals 56a to 56c of the first reflection reading light source 52a extend from the upper surface in the vertical direction of the package body 55, and the terminals 56d to 56f extend from the lower surface In the vertical direction of the package body 55. The electrodes 57a and 57b of the second reflection reading light source 52b and the transmission reading light source 52c are separately positioned in the vertical direction.

Therefore, in the first circuit board 60a of the present embodiment, the length in the width direction is shorter than the length in the vertical direction in the outer shape of the light source connection pads combined. Therefore, the length in the width direction of the mounting portion 62 can be reduced.

Figure 9B:
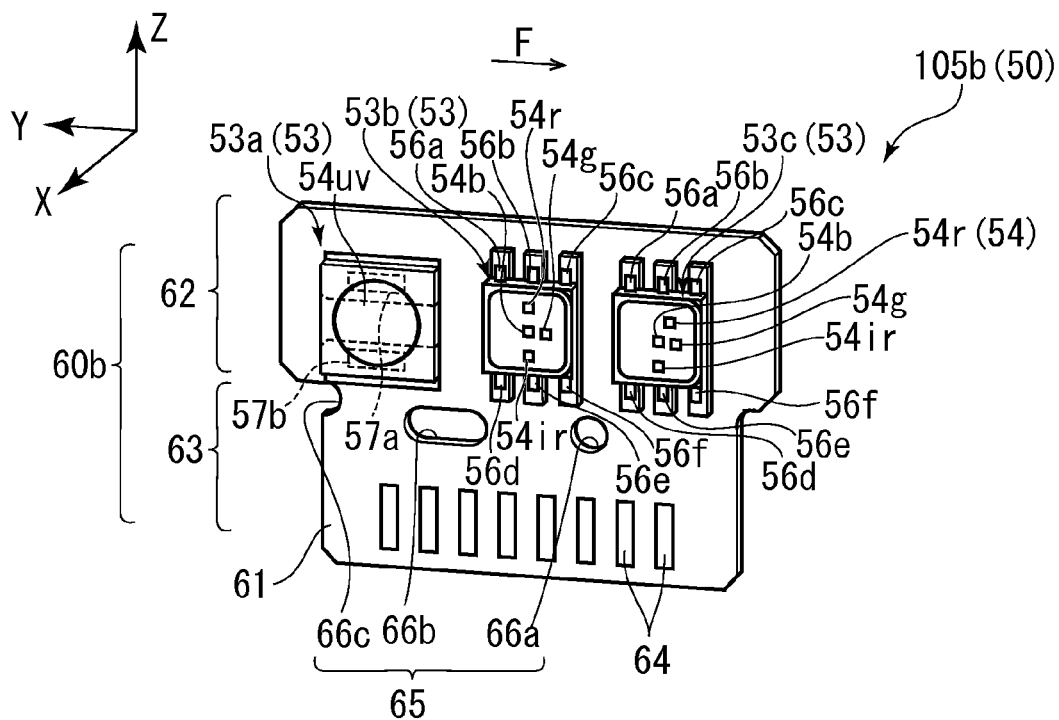
FIG. 9B is a perspective view showing a configuration of a second light source portion of the fourth embodiment.

FIG. 9B is a perspective view showing a configuration of a second light source portion 105b of the present embodiment. As shown in FIG. 9B, the first reflection reading light source 53a, the second reflection reading light source 53b, and the transmission reading light source 53c of the second light source portion 105b are rotated 90 degrees from the first embodiment and mounted on the mounting surface 61. Therefore, in the second circuit board 60b of the present embodiment, the length in the width direction is shorter than the length in the vertical direction in the outer shape of the light source connection pads combined, as in the first light source portion 105a. Therefore, the length in the width direction of the mounting portion 62 can be reduced.

(Fifth Embodiment)

In the first embodiment, the case has been described in which the connecting portion 63 of the first circuit board 60a and the connecting portion 63 of the second circuit board 60b are inserted into the connection hole 42a and the connection hole 42b as the connection portions of the sensor substrate 40, respectively, to connect the first circuit board 60a and the second circuit board 60b to the sensor substrate 40. In the present embodiment, a case in which the connection portions are not hole-shaped will be described. The same components as in the first embodiment are designated with the same reference numerals, and the description will not be repeated.

Figure 10:
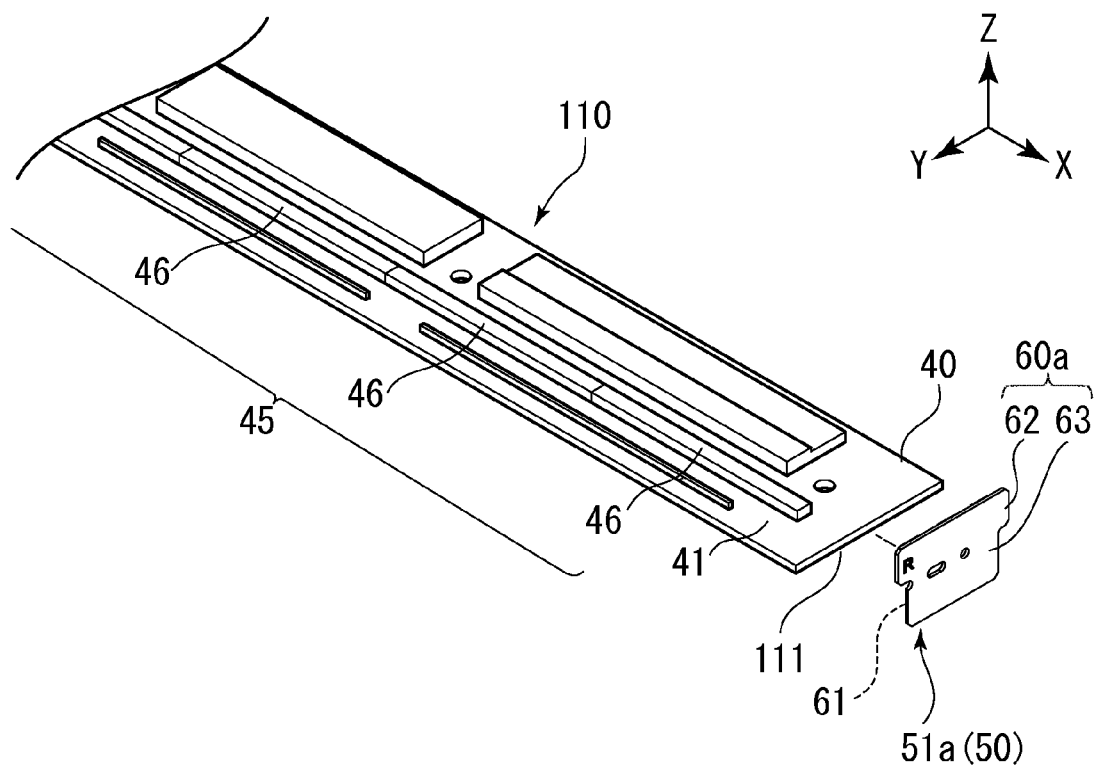
FIG. 10 is a perspective view showing a configuration of a sensor substrate and a first light source portion of a fifth embodiment.

FIG. 10 is a perspective view showing a configuration of a connection portion on one side in the longitudinal direction of a sensor substrate 110 of the present embodiment. A connection portion on the other side in the longitudinal direction of the sensor substrate 110 has the same configuration, and the illustration is omitted.

In the present embodiment, an edge portion 111 on one side of the sensor substrate 110 is a connection portion connected to the connecting portion 63 of the first circuit board 60a. In the state that the lower image sensor unit 10A is assembled, an end face of the age portion 111 and the mounting surface 51 of the first circuit board 60a face each other. In this case, the end face of the edge portion 111 touches the mounting surface 61. However, the end face of the edge portion 111 and the mounting surface 51 may be separated as long as the end face of the edge portion 111 and the mounting surface 61 can be electrically connected.

To assemble the image sensor unit portion 10, the cover glass 13 is fixed to the upper surface of the frame 14, the frame 14 is vertically inverted so that the cover glass 13 serves as a lower surface, and the vertically inverted sensor substrate 110 is housed in the substrate housing portion 17, as in the first embodiment.

Figure 11:
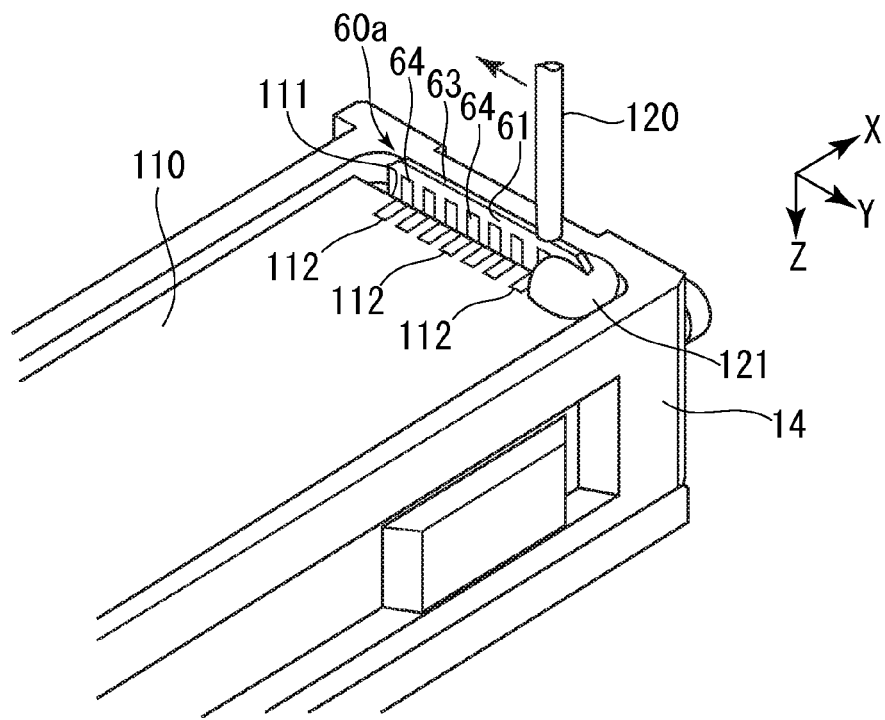
FIG. 11 is a diagram for explaining an assembly method of an image sensor unit of the fifth embodiment.

In this case, the mounting surf the connect portion 63 of the first circuit board 60a faces the end face of the edge portion 111 on one side in the longitudinal direction of the sensor substrate 110 as shown in FIG. 11.

Subsequently, the external connection pads 64 of the first circuit board 60a exposed from the lower surface of the sensor substrate 110 are soldered to external connection pads 112 of the sensor substrate 110.

An adhesive for maintaining the connection is used to bond the sensor substrate 110 and the first circuit board 60a. Specifically, a nozzle 120 is used to apply an adhesive 121 around the connecting portion 63 of the first circuit board 60a exposed from the lower surface of the sensor substrate 110 as shown in FIG. 11.

Figure 12:
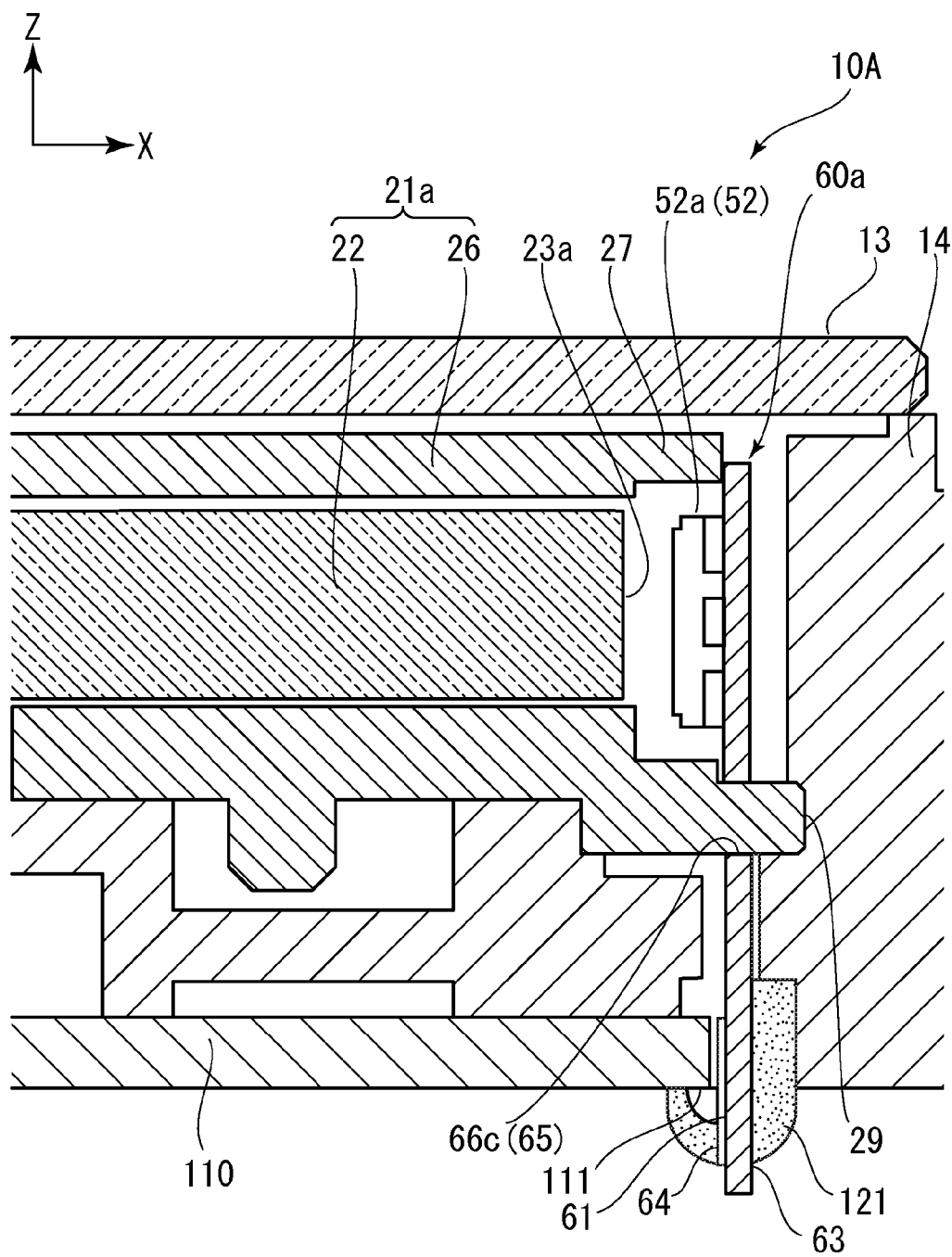
FIG. 12 is a sectional view of a part of a lower image sensor unit of the fifth embodiment.

FIG. 12 is a sectional view on one side in the longitudinal direction of the manufactured image sensor unit portion 10. As shown in FIG. 12, the adhesive 121 is entirely applied between the edge portion 111 of the sensor substrate 110 and the connecting portion 63 of the first circuit board 60a, and the sensor substrate 110 and the first circuit board 60a can be strongly connected. The adhesive 121 is also provided between the first circuit board 60a and the frame 14. Therefore, the connection between the sensor substrate 110 and the first circuit board. 60a is also reinforced by the frame 14 through the adhesive 121. The sensor substrate 110 and the first circuit board 60a may be connected only by the adhesive 121 provided between the first circuit board 60a and the frame 14.

Although the case of connecting the first circuit board 60a and the sensor substrate 110 has been described here, the same applies to the case of connecting the second circuit hoard 60b and the sensor substrate 110.

In this way, since the connection portion of the sensor substrate 110 of the present embodiment is formed by the edge portion 111 instead of forming the connection portion in a hole shape, the area from the connection hole 42a to the end face on one side of the sensor substrate 40 can be omitted from the sensor substrate 40 of the first embodiment.

Therefore, the dimension in the main-scan direction of the sensor substrate 110 can be reduced, and the image sensor unit portion 10 can be downsized.

It is preferable to vertically, not obliquely, form the end face of the edge portion 111 in order to form the external connection pads 112 of the sensor substrate 110 near the first circuit board 60a.

Although the preferred embodiments of the present invention have been described, the present invention is not limited to the embodiments, and various modifications and changes can be made within the scope of the present invention.

Although the case of arranging the light sources on one side and the other side in the longitudinal direction of the light guide portion has been described in the embodiments, the light sources may be arranged only on one side in the longitudinal direction of the light guide portion.

In the first embodiment, the first light source 52a that emits RGB and IR is arranged on one side in the longitudinal direction of the first reflection reading light guide portion 21a, and the first light source 53a that emits UV is arranged on the other side. The case of arranging the second light source 52b that emits UV on one side in the longitudinal direction of the second reflection reading light guide portion 21b and arranging the second light source 53b that emits RGB and IR on the other side has been described. However, the arrangement is not limited to this as long as the lights (RGB, IR, and UV here) with emission wavelengths according to the specifications can be emitted to the bill S through the first reflection reading light guide portion 21a or the second reflection reading light guide portion 21b.

The case of arranging the third light source 52c that emits UV on one side in the longitudinal direction of the transmission reading light guide portion 31 and arranging the third light source 53c that emits RGB on the other side has been described in the first embodiment. However, the arrangement is not limited to this as long as the lights (RGB, IR, and UV here) with emission wavelengths according to the specifications can be emitted to the bill S through the transmission reading light guide portion 31. When there is no need to emit IR and UV, light sources without light emitting elements that emit IR and UV can be used, or light emitting elements that emit IA and UV can be replaced with light emitting elements that emit RGB in the light sources.

Although the case in which the lower image sensor unit 10A and the upper image sensor unit 10B have the same configuration and are disposed symmetric about the center line Oc shown in FIG. 1 has been described in the first and second embodiments, the arrangement is not limited to this. More specifically, the lower image sensor unit 10A and the upper image sensor unit 10B may not have the same configuration. For example, the transmission reading illumination portion 12 may be included only on one side.

According to the present invention, a circuit board including a plurality of light sources mounted on the same mounting surface can be connected to a sensor substrate to easily assemble an image sensor unit.

It should be noted that the above embodiments merely illustrate concrete examples of implementing the present invention, and the technical scope of the present invention is not to be construed in a restrictive manner by these embodiments. That is, the present invention may be implemented in various forms without departing from the technical spirit or main features thereof.

What is claimed is:

1. An image sensor unit comprising:
   a circuit board;
   a plurality of light sources each comprising a light emitting element and disposed on a same side of the circuit board;
   a plurality of elongated light guides disposed parallely to each other, and having light incident surfaces each disposed at one longitudinal end thereof, to guide light from the plurality of light sources to an illuminated body;
   a sensor substrate having a first connecting portion disposed at one end thereof; and
   an image sensor that converts light from the illuminated body to an electric signal and disposed on the sensor substrate;
   wherein the circuit board is disposed at the one longitudinal end of the plurality of elongated light guides so that the plurality of light sources face the light incident surfaces disposed at the one longitudinal end of the plurality of elongated light guides, and
   wherein the circuit board has a second connecting portion including a plurality of first external connection pads disposed at one end of the circuit board, the second connecting portion connected to the first connecting portion disposed at the one end of the sensor substrate.

2. The image sensor unit according to claim 1, wherein:
   the first connecting portion includes an elongated connection hole, and
   the circuit board is connected to the sensor substrate by inserting the second connecting portion into the elongated connection hole.

3. The image sensor unit according to claim 1, wherein:
   the first connecting portion includes an edge portion on one side of the sensor substrate, and
   the circuit board is connected to the sensor substrate by bonding the second connecting portion and the edge portion.

4. The image sensor unit according to claim 1, further comprising:
   a plurality of light guide holding members that hold the plurality of elongated light guides respectively,
   wherein the light guide holding members include projections protruding toward the circuit board respectively, and
   wherein the light guide holding members position the circuit board by inserting the projections into insertion holes formed on the circuit board.

5. The image sensor unit according to claim 1, wherein:
   the circuit board comprises a mounting portion provided with a plurality of light source connection pads corresponding to the plurality of light sources respectively, and
   the plurality of light source connection pads are disposed so that a length in a vertical direction orthogonal to a width direction is shorter than a length in the width direction in an outer shape of the plurality of light source connection pads combined.

6. The image sensor unit according to claim 1, wherein:
   the circuit board comprises a mounting portion provided with a plurality of light source connection pads corresponding to the plurality of light sources respectively, and
   the plurality of light source connection pads are each disposed so that a length in a width direction is shorter than a length in a vertical direction orthogonal to the width direction in an outer shape of the plurality of light source connection pads combined.

7. The image sensor unit according to claim 1, wherein:
   the circuit board comprises a first circuit board and a second circuit board,
   the first circuit board has at least one first light source, among the plurality of light sources, disposed on the same side thereof,
   the second circuit board has at least one second light source, among the plurality of light sources, disposed on the same side thereof,
   the first circuit board is disposed facing one end side of the plurality of elongated light guides so that the at least one first light source each face the one end side of one of the plurality of elongated light guides, and
   the second circuit board is disposed facing an opposite end side of the plurality of elongated light guides so that the at least one second light source each face the opposite end side of one of the plurality of elongated light guides.

8. The image sensor unit according to claim 7, wherein an outer shape of the first circuit board and an outer shape of the second circuit board are mirror-symmetric.

9. The image sensor unit according to claim 1, wherein the plurality of elongated light guides include at least three elongated light guides.

10. The image sensor unit according to claim 1, wherein the plurality of light sources comprise the light emitting elements that emit light with emission wavelengths of visible light, infrared light, and ultraviolet light.

11. An image reading apparatus comprising:
    an image sensor unit comprising:
       a circuit board;
       a plurality of light sources each comprising a light emitting element and disposed on a same side of the circuit board;
       a plurality of elongated light guides disposed parallely to each other, and having light incident surfaces each disposed at one longitudinal end thereof, to guide light from the plurality of light sources to an illuminated body;
       a sensor substrate having a first connecting portion disposed at one end thereof; and
       an image sensor that converts light from the illuminated body to an electric signal and disposed on the sensor substrate;
       wherein the circuit board is disposed at the one longitudinal end of the plurality of elongated light guides so that the plurality of light sources face the light incident surfaces disposed at the one longitudinal end of the plurality of elongated light guides, and
       wherein the circuit board has a second connecting portion including a plurality of first external connection pads disposed at one end of the circuit board, the second connecting portion connected to the first connecting portion disposed at the one end of the sensor substrate; and
    a transfer portion that relatively transfers the image sensor unit and the illuminated body.

12. A paper sheet distinguishing apparatus comprising:
    an image sensor unit comprising:
       a circuit board;
       a plurality of light sources each comprising a light emitting element and disposed on a same side of the circuit board;
       a plurality of elongated light guides disposed parallely to each other, and having light incident surfaces each disposed at one longitudinal end thereof, to guide light from the plurality of light sources to an illuminated body;

a sensor substrate having a first connecting portion disposed at one end thereof; and an image sensor that converts light from the illuminated body to an electric signal and disposed on the sensor substrate;

wherein the circuit board is disposed at the one longitudinal end of the plurality of elongated light guides so that the plurality of light sources face the light incident surfaces disposed at the one longitudinal end of the plurality of elongated light guides, and wherein the circuit board has a second connecting portion including a plurality of first external connection pads disposed at one end of the circuit board, the second connecting portion connected to the first connecting portion disposed at the end of the sensor substrate;

a transfer portion that transfers a paper sheet as the illuminated body;

a storage portion that stores reference data as a reference for distinguishing the paper sheet; and a comparison portion that compares image information read by the image sensor unit and the reference data stored in the storage portion to distinguish the paper sheet.

13. The image sensor unit according to claim 1, wherein the circuit board has a third connecting portion including a plurality of second external connection pads disposed at the other end of the circuit board, wherein the third connecting portion is electrically connected to the second connecting portion, and wherein the plurality of light sources are electrically connected to the third connecting portion.

* * * * *